US006847847B2

(12) United States Patent
Nisch et al.

(10) Patent No.: US 6,847,847 B2
(45) Date of Patent: Jan. 25, 2005

(54) RETINA IMPLANT ASSEMBLY AND METHODS FOR MANUFACTURING THE SAME

(75) Inventors: Wilfried Nisch, Tübingen (DE); Alfred Stett, Reutlingen (DE); Markus Schubert, Tübingen (DE); Michael Graf, Leonberg (DE); Heinz Gerhard Graf, Magstadt (DE); Hugo Hämmerle, Tübingen (DE); Eberhart Zrenner, Tübingen (DE); Martin Stelzle, Reutlingen (DE); Helmut Sachs, Regensburg (DE)

(73) Assignee: Eberhard-Karls Universitat Tubingen, Universitatsklinikum, Tubingen (DE)

( * ) Notice: Subject to any disclaimer, the term of this patent is extended or adjusted under 35 U.S.C. 154(b) by 122 days.

(21) Appl. No.: 10/011,641

(22) Filed: Nov. 7, 2001

(65) Prior Publication Data

US 2002/0198573 A1 Dec. 26, 2002

Related U.S. Application Data

(63) Continuation-in-part of application No. PCT/EP00/03962, filed on May 3, 2000.

(30) Foreign Application Priority Data

May 7, 1999 (DE) ........................................ 199 21 398
Jul. 6, 1999 (DE) ........................................ 199 31 083

(51) Int. Cl.[7] .............................. A61N 1/36; A61F 2/14
(52) U.S. Cl. ......................................... 607/54; 623/4.1
(58) Field of Search ............................ 607/53–54, 141, 607/116, 118; 623/4.1, 11

(56) References Cited

U.S. PATENT DOCUMENTS

| 2,760,483 A | 8/1956 | Tassicker .................... 623/6.63 |
| 4,628,933 A | 12/1986 | Michelson .................... 607/53 |
| 5,147,284 A | 9/1992 | Fedorov et al. ................. 600/9 |

(List continued on next page.)

FOREIGN PATENT DOCUMENTS

| DE | 44 38 201 | 5/1996 | ............. A61F/9/00 |
| DE | 197 41 487 | 4/1999 | ........... A61F/9/007 |

(List continued on next page.)

OTHER PUBLICATIONS

Jesinger, et al., "Flexible Electrode Array for Retinal Stimulation" *Proceedings of the Annual International Conference of the IEEE Engineering in Medicine and Biology Society* vol. 14, Oct. 29–Nov. 1, 1992 pp. 2393.

(List continued on next page.)

*Primary Examiner*—Carl Layno
(74) *Attorney, Agent, or Firm*—Knobbe, Martens, Olson & Bear, LLP

(57) ABSTRACT

A retina implant including a chip adapted to be implanted into the interior of eye in subretinal contact with the retina. The chip has a plurality of pixel elements on a side thereof facing the lens for receiving an image projected into the retina and a plurality of electrodes for stimulating retina cells. The implants further includes a receiver coil for inductively coupling thereinto electromagnetic energy. The receiver coil coupled to a means for converting an alternating voltage induced into the receiver coil in a direct voltage suited for supplying the chip. The receiver coil is configured as a component separate from the chip, and for being positioned on the eye ball outside the sclera. The chip is connected to the receiver coil via a connecting lead which, in the implanted condition interconnects the interior and the exterior of the eye ball.

49 Claims, 3 Drawing Sheets

U.S. PATENT DOCUMENTS

| | | | | |
|---|---|---|---|---|
| 5,556,423 A | * | 9/1996 | Chow et al. | 623/6.63 |
| 5,935,155 A | | 8/1999 | Humayun et al. | 607/54 |
| 6,298,270 B1 | | 10/2001 | Nisch et al. | 607/54 |

FOREIGN PATENT DOCUMENTS

| | | | | |
|---|---|---|---|---|
| WO | 98/17343 A1 | 4/1998 | | A61N/1/05 |
| WO | 99/15119 | 4/1999 | | A61F/9/007 |
| WO | 00/67676 | 11/2000 | | A61F/2/14 |
| WO | WO 00/67838 | * 11/2000 | | A61N/1/36 |

OTHER PUBLICATIONS

Rouch, W., "Envisioning an Artificial Retina" *Science* vol. 268, May 5, 1995 pp. 637–638.

Trieu, H.K., et al., "Flexible Slicon Structures for a Retina Implant" *IEEE* 1998 pp. 515–519.

* cited by examiner

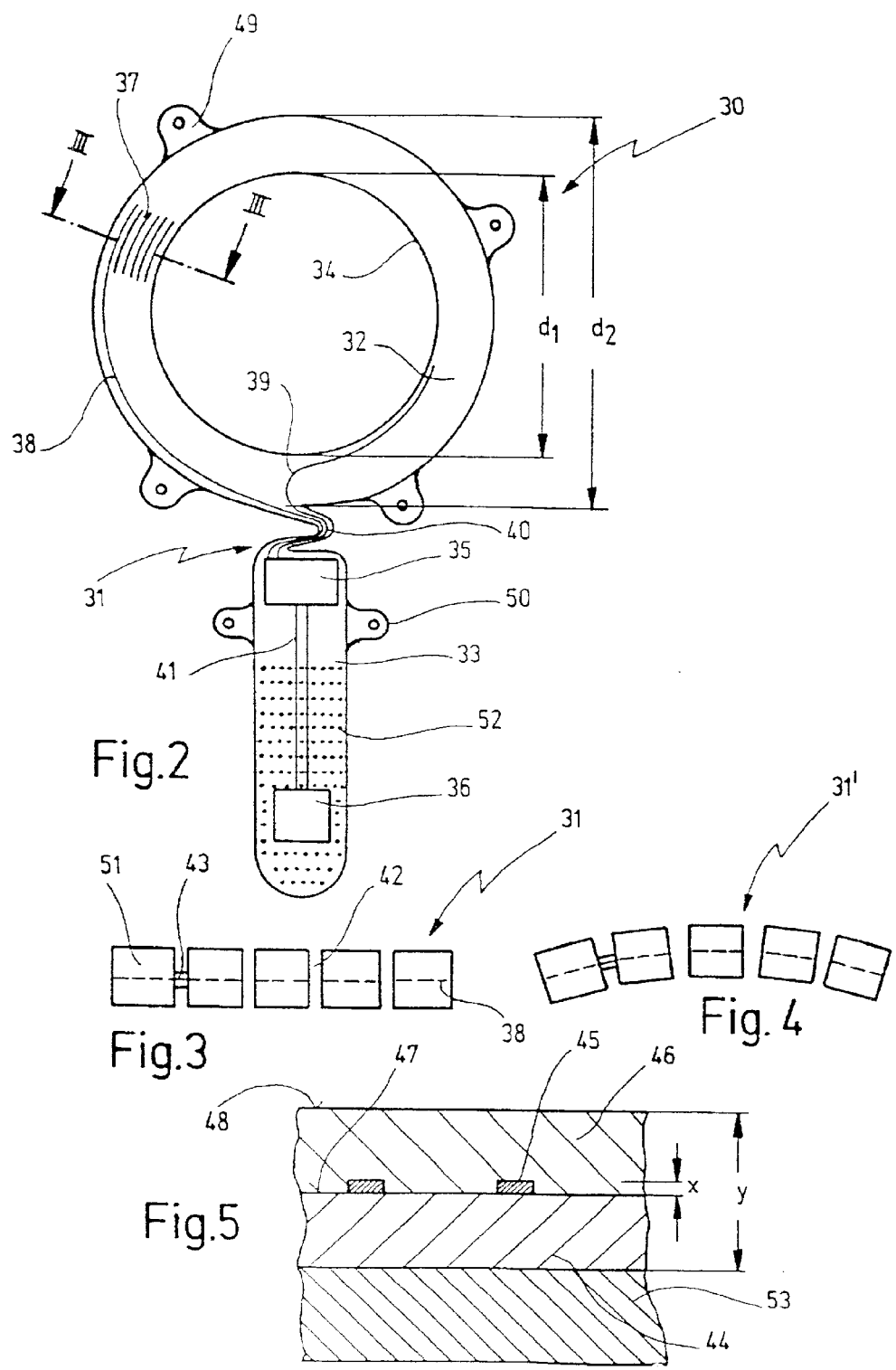

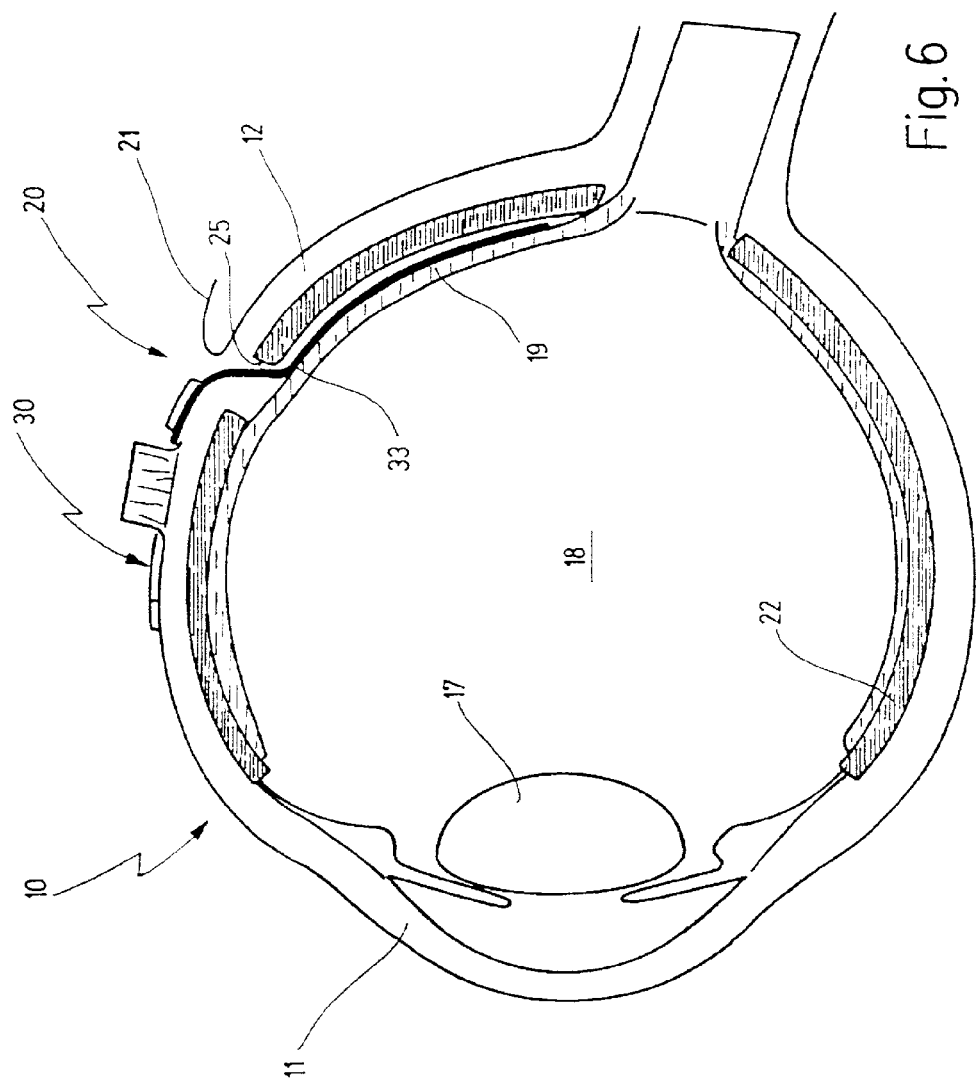

RETINA IMPLANT ASSEMBLY AND METHODS FOR MANUFACTURING THE SAME

RELATED APPLICATIONS

This application is a continuation-in-part of the PCT application PCT/EP00/03962 filed 3 May 2000 entitled "A RETINA IMPLANT AND A METHOD FOR MANUFACTURING SAME" and claims the benefits of the German Applications 199 21 398.4 filed 7 May 1999, and 199 31 083.1 filed 6 Jul. 1999.

FIELD OF THE INVENTION

The invention relates to a retina implant having a chip for subretinal implantation, and comprising a receiver coil for inductively coupling thereinto electromagnetic energy, the coil being connected to means for converting an alternating voltage induced into the receiver coil into a direct voltage suited for supplying the chip.

The invention, further, is related to a method for manufacturing a retina implant as specified before.

Implants of that kind are generally known.

BACKGROUND OF THE INVENTION

Recently, retina implants have been developed that are intended to be used for the treatment of patients whose viewing ability has gone lost entirely or in part due to retinal defects. As a matter of principle, a light-sensitive chip shall be implanted into the subretinal space below the retina. The chip is provided with a plurality of pixel elements receiving an image projected on the retina through the still intact lens of the eye, for converting same into electrical signals and for further converting same into electrical stimuli via a plurality of stimulation electrodes to stimulate the retinal cells adjacent the chip, in order to reconstruct or improve vision of blind or partially blind patients.

U.S. Pat. No. 4,628,933 discloses a retina implant which, however, is not intended to be used for subretinal implantation but for epiretinal implantation instead, i.e. the light-sensitive chip shall not be implanted into the subretinal space but directly onto the surface of the retina. The stimulation electrodes, therefore, are not provided on the side of the chip facing the lens but on its rear side instead.

It has been found out that for subretinal implants as well as for epiretinal implants it is necessary to feed external energy in order to actively amplify the received light signals and for converting same into stimulation signals for the adjacent cells.

For that purpose, U.S. Pat. No. 4,628,933 suggests to transmit energy to the implant via electromagnetic induction. For that purpose, a receiver coil is wound around the periphery of the implant chip. By means of the receiver coil, radiofrequency energy having been transmitted from an external source of energy which, for example, may be located in an eyeglass frame, is received and is transformed into electrical energy for supplying the chip.

Considering that such a coil must be provided with a sufficient number of windings, must have a considerable coil diameter for an effective coupling of radiofrequency energy and, further, appropriate installations must be provided for rectifying and smoothening the induced alternating current, a chip of that kind would hardly be adapted to be implanted into the human eye due to its substantial dimensions.

For that purpose, subretinal implants have been developed recently which have not been supplied via rf coupling of electromagnetic energy but via invisible infrared radiation which was converted into electrical energy by means of an appropriate photovoltaic layer.

A subretinal implant of the type specified before is disclosed e.g. in WO 98/17343.

However, it must be considered to be disadvantageous in that case that for operating the implant, infrared radiation must continuously be irradiated into the eye.

It is, therefore, an object underlying the invention to provide an improved retina implant being supplied with electromagnetic energy via inductive coupling and which may be implanted into the subretinal space simply and without the risks of complications.

Moreover, a method for manufacturing such a retina implant shall be provided.

SUMMARY OF THE INVENTION

According to a retina implant as specified at the outset, this object is achieved in that the receiver coil is configured to be received and positioned on the eyeball outside the sclera.

By doing so, it is possible to utilize a sufficiently dimensioned receiver coil positioned outside the eyeball which can be inserted preferably by means of surgical methods avoiding to guide the implant through the vitreous body of the eye.

As the receiver coil is affixed to the sclera outside the eye, the chip that has to be implanted into the subretinal space may be dimensioned appropriately which is of particular advantage for an implantation into the subretinal space. In contrast, the receiver coil may be provided with a sufficiently large cross-section and a sufficiently high number of windings without incurring disadvantageous effects.

In a preferred embodiment of the invention, the receiver coil, the chip as well as connecting leads leading to the chip are housed within a flat plastic material body.

This enables to utilize a compact design and low-risk implantation techniques by effecting a sclera incision on the lateral portion in the area of the eye equator. The end of the flat plastic material body on which the chip is located, may be brought into the subretinal space via the incision. The operation that may be used insofar is partially similar to the surgical technique described in German disclosure document DE 197 41 487 A1.

According to a preferred embodiment of the invention, the converting means is configured as a unit separate from the chip, the unit being adapted to be positioned on the eyeball outside the sclera.

By this feature, the portion of the entire retina implant to be implanted into the subretinal space is made still smaller because the converter means must be provided with a rectifier and with smoothing capacitors which require a certain space and, hence, may not be directly combined with the chip without substantially increasing the dimensions thereof.

By using such a design, that portion of the implant to be implanted into the subretinal space of the eyeball is made still smaller so that that portion of the plastic material body may be configured as a thin foil and the chip may be integrated into a terminal end thereof.

In a preferred embodiment of the invention, the plastic material body comprises an annular portion having a central opening, the annular portion being adjoined by a flat extension.

By doing so, the receiver coil may be integrated into the annular portion of the plastic material body in a most suitable manner, whereas the chip may be provided at the end of the flat extension.

According to still another preferred embodiment of the invention, the annular portion is dimensioned as to enclose the lateral straight eye muscle rudiment.

This measure has the advantage that a particularly preferable arrangement and positioning of the receiver coil on the eye is achieved. For the implantation, the eye muscle must be severed, however, may thereafter be sewed together again which, in view of modern surgical techniques, does not present a problem at all.

In such an arrangement, the excitation coils for the energy supply may be arranged in the area of the temples, for example on an eyeglass frame.

In contrast, the converting means is comprised within the plastic material body in a position adjacent the receiver coil.

By doing so, the converting means which requires a certain space is positioned most advantageously.

According to still another embodiment of the invention, the receiver coil comprises windings integrated into the annular portion and being, preferably, configured in a spiralled pattern.

By doing so, the receiver coil may advantageously be integrated into the annular portion of the plastic material body.

In a supplemental improvement of this embodiment, the annular portion is subdivided into a plurality of sections in a circumferential direction, the sections being separated from each other by gaps and being electrically and mechanically interconnected.

This feature allows to improve the flexibility of the annular portion so that the annular portion of the plastic material body may perfectly be applied to the bulged surface of the eye even if it consists of a material of relatively high tensile strength.

Insofar, the sections may be interconnected with each other by a fin in a radial direction, or the sections may be made to adhere each other in a spiralled configuration.

Preferably, the individual sections each have a plurality of windings and are interconnected in a radial direction via fins which also carry the electrical connections between neighbored windings.

By doing so, it is possible to obtain a particularly good flexibility and adaptation to the bulged surface of an eyeball, wherein the annular portion may first be manufactured as a planar body and may subsequently be brought into the desired bulged shape.

According to still another modification of the annular portion of the plastic material body, it may have a meander shape in order to obtain an improved flexibility.

According to still another embodiment of the invention, strain relief means are provided at least between the converter means and a connection lead leading to the chip or to the receiver coil.

The strain relief means may, for example, be obtained by a meander-shaped configuration substantially in the area between the annular portion and the flat extension where the converter means is received or in an area immediately adjacent the converter means.

By doing so, the electrical interconnection between the receiver coil, the converter means and the chip are protected against hazardous influences which may result from the continuous movement of the eyeball, so that even years after an implantation a reliable voltage supply for the implanted chips is guaranteed.

In a preferred embodiment of the invention, the receiver coil has a number of windings of about between 50 and 200, preferably about 100 windings.

With such a winding number, an appropriate energy transmission and a sufficient voltage at the receiver coil may be guaranteed.

A receiver coil of that kind may be operated in combination with an external transmitter coil at a frequency of 1 MHz, when the transmitter coil has about 1000 windings with a diameter of about 50 mm and is attached to, for example, an eyeglass frame.

In a preferred embodiment of the invention, the receiver coil has an outer diameter of about between 12 and 20 mm and an inner diameter at the opening of about between 8 and 16 mm.

With such dimensions, an advantageous adaptation to the anatomy of the human eye may be guaranteed.

In still another preferred embodiment of the invention, the flat extension is provided with a plurality of perforations.

These perforations, for example, may be arranged along an array of about between 0.1 and 1 mm width and have a diameter in the area of about between 20 and 200 $\mu$m.

This allows the diffusion of nutrients and oxygen between the pigment epithelium and the retina, so that disadvantages that could be caused by implanting an impermeable item are avoided.

According to still another preferred embodiment of the invention, the chip is embedded in the flat extension, the active side of the chip lying open at the surface for stimulating cells.

This makes sure that the chip may be advanced in a lateral direction into the subretinal space during an appropriate surgical technique utilizing a sclera incision in the area of the lateral eye muscle.

According to still another preferred embodiment of the invention, the flat plastic material body is provided with lugs for affixing the plastic material body to the eyeball.

This ensures a safe seating in the desired position on the eyeball. The lugs may either be provided at the annular portion as well as in the flat extension, preferably in the area where the converter means are received.

According to another embodiment of the invention, the converter means comprises means for processing an information signal transmitted together with the electromagnetic energy, in particular for processing a referenced signal indicative for ambient light intensity or brightness.

This allows an adaptation of the output signal amplitude of the chip under varying ambient light intensity or brightness conditions. By doing so, the performance of the implanted chip may be improved significantly.

In a preferred embodiment of the invention, the flat plastic material body is generated on an auxiliary substrate and may be separated therefrom thereafter.

By doing so, the manufacturing method is significantly simplified.

When doing so, the strip conductors are preferably generated on the surface by means of thin film methods (vapor deposition or sputtering) and are then microstructured photolithographically.

By using these well-established manufacturing process, a high precision and quality may be guaranteed.

The object underlying the invention is, further, achieved by a method for manufacturing a retina implant having a chip for subretinal implantation, and comprising a receiver coil for inductively coupling thereinto electromagnetic energy, means for converting an alternating voltage induced into the receiver coil into a direct voltage suited for supplying the chip, the method comprising the steps of:

manufacturing a flat plastic material body having an annular portion with a central opening, the annular portion being adjoined by a flat extension, depositing metallic strip conductors on a surface of the annular portion in a spiralled configuration for making windings of the receiver coil and for creating connecting leads between the receiver coil, the converter means and the chip, affixing the chip and the converter means to the plastic material body, depositing an isolation layer over the metallic strip conductors.

According to the invention, one can manufacture a retina implant accordingly, having a thin foil-type extension with the chip to be implanted, the retina implant being configured as an integral flat unit which may be implanted in a particularly advantageous manner and with a minimum of potential complication and which, further, has a long lifetime over a sufficiently long period of time.

According to an improvement of the invention, the converter means is affixed to the plastic material body by gluing, by bonding to the metallic strip conductors and/or by injection-molding same with a plastic material mass.

By doing so, a long-lasting and permanent attachment of the converter means on the plastic material body may be achieved, together with a good sealing to the exterior.

According to a preferred embodiment of the invention, the plastic material body is manufactured from polyimide, polymethylmetacrylate (PMMA) or epoxy resin. Likewise, these materials may be utilized for embedding the chip and/or for embedding the converter means by injection-molding.

These materials are well-suited from a biological point of view, wherein polyimide and PMMA are particularly preferred.

The plastic material body together with the isolation layer is manufactured with a thickness of about between 5 and 15 micrometers, preferably about 10 micrometers.

Accordingly, the receiver coil as well as the chip and the necessary leads may be housed in a thin foil-type body which is well-suited for implantation purposes.

Accordingly, the strip conductors have a thickness of about between 0.5 and 2 micrometers, preferably of about 1 micrometer.

These dimensions have turned out to be sufficient for a reliable electrical connection.

The strip connectors are preferably generated by vapor deposition or sputtering, respectively, allowing an advantageous manufacture. Preferably, they consist of gold, titanium, platinum, iridium, aluminum, or copper.

It goes without saying that the features mentioned before and those that will be mentioned hereinafter cannot only be used in the particularly given combination but also in other combinations or alone without leaving the scope of the present invention.

BRIEF DESCRIPTION OF THE DRAWINGS

Further features and advantages of the invention become apparent from the subsequent description of preferred embodiments with reference to the drawings.

FIG. 2 shows a view on the retina implant in a slightly modified embodiment, on an enlarged scale;

FIG. 3 is a cross-sectional view on the annular area of the implant along the line III—III on an enlarged scale;

FIG. 4 shows the annular area of FIG. 3 when assuming a curved shape under a bending load;

FIG. 5 shows a portion of the annular area of the implant, on a still more enlarged scale as compared to FIG. 3, and FIG. 6 shows a schematic cross-sectional view through an eye with the introduced implant.

DETAILED DESCRIPTION OF THE PREFERRED EMBODIMENTS

Figure 1:
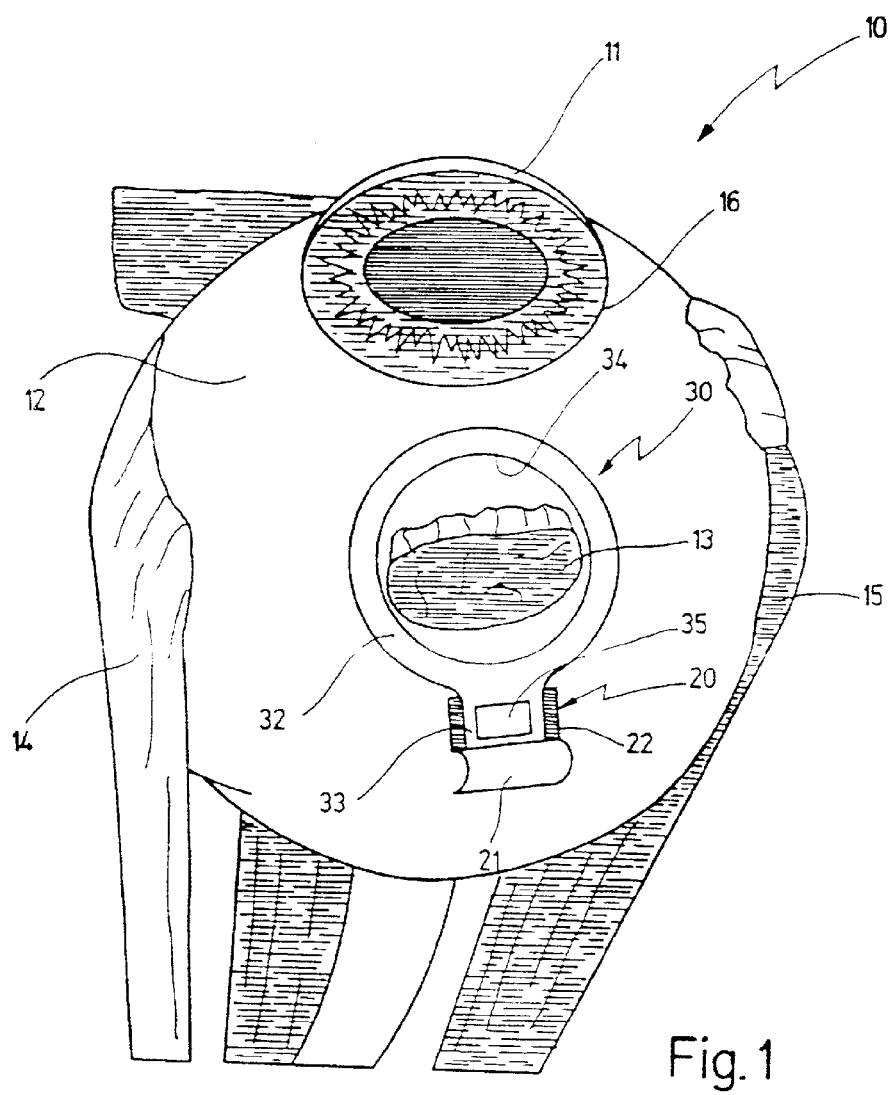
FIG. 1 shows a perspective view of a dissected eye with introduced retina implant.

In FIGS. 1 and 6 an eyeball into which an implant according to the present invention shall be introduced, is designated as a whole by 10. Eyeball 10, at its front side, has a cornea 11 and, further, a sclera 12. The limbus corneae, i.e. the rim of cornea 11, is designated by 16 in FIG. 1. Moreover, FIG. 1 shows lateral eye muscles 14 and 15.

At the front portion of eyeball 10, lateral eye muscle 13 was severed by a cut. A retina implant according to the present invention, being designated as a whole by 30, has an annular portion 32 and an extension 33 adjoining the latter. A chip for subretinal implantation is located at the outer terminal end of extension 33, as may be seen in further detail in FIG. 2. FIG. 1 shows that the retina implant was positioned around lateral eye muscle 13 with its annular portion 32 and was pushed into the subretinal space with its flat extension 33 through a sclera incision 20.

The design and the manufacture of the retina implant will be described hereinafter in further detail with reference to FIGS. 2 through 5.

FIG. 2 shows the retina implant in a top plan view and on an enlarged scale. As a modification with respect to the embodiment of FIG. 1, a strain relief is, further, provided, as will be explained hereinafter.

Retina implant 30 comprises a receiver coil 37 for receiving electromagnetic energy (rf energy), irradiated thereinto, a converter means 35, for rectifying and smoothening alternating current induced into receiver coil 37 and, as the case may be, stabilizing on a predetermined voltage, as well as the chip 36 for subretinal implantation.

Converter means 35 which, due to the necessary smoothing capacitors, has a certain demand for space, is, therefore, configured as a unit separated spatially from chip 36. Converter means 35 is positioned at the beginning of flat extension 33 adjacent annular area 32. Converter means 35 consists, for example, of rectifiers, smoothing capacitors and rechargeable thin film batteries, respectively, and a voltage stabilizer. Moreover, it may comprise components for decoding and processing of information signals transmitted together with the electromagnetic energy, for example of reference signals indicative for ambient brightness.

The retina implant comprises a flat plastic material body 31 consisting, preferably, of polyimide. Plastic material body 31 receives various components or these components are affixed thereto. A central opening or recess is provided within annular area 32 of plastic material body 31. Central opening 34 has a diameter $d_1$ of about between 8 and 16 mm. The outer diameter $d_2$ of the annular portion is about between 12 and 20 mm. Receiver coil 37 is received within annular portion 32. The windings thereof are indicated as an example at 38 in FIG. 2. The ends of receiver 37 which, as may be taken from FIG. 2, may comprise a zig-zag-shaped or meander-shaped tongue, are connected to converter means 35. Converter means 35 is connected to chip 36 via connection leads 41. Chip 36 is embedded into plastic material body 31 at the outer end of flat extension 33. It goes without saying that its active surface which is supposed to stimulate cells, lies free. In order to simplify the attachment of implant 30 on eyeball 10 in its final position, annular portion 32 and flat extension 33 are provided with lugs 49 and 50, respectively. As may further be taken from FIG. 2, flat extension 33 in its portion being intended to be pushed into the subretinal space at a later point in time, is provided with a plurality of perforations 52. The perforations 52 are preferably arranged along an array of about between 0.1 and 1 mm width and have a diameter of about between 20 and 200 µm. By doing so, a diffusion of nutrients and oxygen between the pigment epithelium and the retina in enabled, thus avoiding negative effects that might result if the implant consisted of an impermeable material.

Annular portion 33 receiving receiver coil 37 is preferably subdivided into a plurality of ring-shaped sections 51 in a circumferential direction, as may be seen from FIGS. 3 and 4. Sections 51 are arranged coaxially one relative to the other, are separated by gaps 42 and are mechanically and electrically interconnected via radial fins 43.

Each of these sections 51 contains a plurality of windings 38 and has, for example, a width of the order of about 0.5 mm, whereas the entire width is of the order of between 3 and 4 mm.

FIG. 3, as an example, shows an individual radial fin 43 between the two outer sections 51. Radial fin 43 mechanically connects the two adjacent sections 51 and also allows the electrical connection between neighbored windings 38. The connection to inner sections 51 is likewise effected through radial fins 43 which are preferably arranged at other positions of the annular portion in an angularly offset manner for obtaining a maximum flexibility of receiver coil 37 because plastic material body 31, as will be explained hereinafter, is manufactured as a planar body which, however, shall be applied to the surface of the bulged eyeball without folds or wrinkles and, hence, consists of a plastic material. Additionally, it is possible to bring the isolated sections 51 into a spherical shape after the plastic material body has been fully manufactured, with the spherical shape corresponding to the bulge of the eyeball. It may, for example, be fixated in this bulged shape by molding with silicon, so that the manipulation is simplified during the subsequent implantation.

The retina implant may, for example, be manufactured as follows:

First, a thin plastic material layer 44 (see FIG. 5), that may consist, for example, of polyimide, PMMA or epoxy resin, is laminated or spun onto a planar auxiliary substrate 53, for example a wafer of glass, silicon or ceramic. The auxiliary substrate 53 may, for example, also be a metal foil.

After having generated the thin plastic material layer or foil 44 on the surface of auxiliary substrate 53, metallic strip conductors 45 are generated on the surface of foil 44. For that purpose, the metal, for example gold, titanium, platinum, iridium, aluminum or copper, is vapor-deposited or sputtered onto the surface. Thereby, all metallic strip conductors 45, i.e. the windings 38 of receiver coil 37, the connections between the individual sections 51 of receiver coil 37, the connection leads leading to the converter means 35 via strain relief 40 as well as connection leads 41 into connecting converter means 35 and chip 36, which is finally effected by a subsequent photolithographic microstructuring. A bridge 39 extending from the inner end of receiver coil 37 to its outside must be connected separately. Chip 36 and converter means 35 are affixed to surface 47 of foil 44, for example by conductive gluing or bonding. An isolating layer is deposited for entirely isolating strip conductors 45. The isolating layer may consist of the same plastic material as the plastic material that had first been deposited on auxiliary substrate 53, i.e. polyimide or PMMA.

Subsequently, the body that has so been generated is separated again from auxiliary substrate 53. Depending on the geometric conditions, chip 36 and converter means 35 may be attached to the plastic material body 31 by conductive gluing or bonding after depositing isolation layer 46 onto foil 44.

The gaps 42 between neighbored sections 51 of receiver coil 47 and the meander-shaped strain relief 40 may also be generated in the course of the photolithographic microstructuring.

In contrast, perforations 52 within flat extension 33 are preferably generated by laser drilling.

The individual sections of receiver coil 37 may, further, be molded with silicon to assume a spherical shape being adapted to the bulge to the bulge of an eyeball.

Metallic strip conductors, preferably, have a thickness of about between 0.5 and 2 micrometers, preferably of about 1 micrometer.

After the depositing of isolating layer 46, receiver coil 37 together with foil 44 have a combined thickness y of about 10 micrometers.

Retina implant 30 may be implanted as follows:

After opening the conjunctiva at the rim of cornea 11 at the temple-oriented portion of eyeball 10, a rein thread is applied and the eye is rolled to the inside. The conjunctiva is then shifted laterally, as a lobe as the case may be. A holding thread is applied to the muscle rudiment at the rudiment of the straight lateral eye muscle 13 and the muscle is then severed and flipped laterally together with the holding thread. A sclera incision 20 is then made into the sclera somewhat below the lateral eye muscle, either above or, as shown in FIG. 1, slightly below eye muscle 13. A small quadrangular lobe 21 is then cut in a wing shape and is flipped downwardly.

Holding threads are now applied through the corners of lobe 21 and the lobe is then flipped rearwardly as shown in FIG. 1. Under the application of haemostatic agents, the choroid 22 below sclera 12 and the pigment epithelium are now opened along a slit (see FIG. 6) without perforating the retina 19 itself. The end of the extension 33 carrying chip 36 is now pushed into the choroid slit and advanced into the subretinal space, as the case may be under the control of a fiber optic, until about four fifth of the extension are within the eye 10 and the end thereof together with chip 36 have assumed their final position. As the case may be, the channel may be opened before with a flexible plastic material spatula similar to the extension of retina implant 30 by lifting retina 19 somewhat away from the pigment epithelium.

As soon as the terminal end carrying chip 36 has assumed its final position in the macula area, it is affixed in that position on the sclera by pulling two plastic material threads through the small perforated holes in the lugs 50 at extension 33 and by attaching same on the sclera with individual knots. The annular portion 32 together with receiver coil 37 is similarly attached by means of two more individual head seams drawn through perforations on the lugs 49 of the receiver coil 37 opposite extension 33. Receiver coil 37 is positioned such that the root of lateral straight eye muscle 13 on its eyeball side is located within opening 34 of annular portion 32.

Thereafter, wing-shaped lobe 21 of sclera 11 is closed at its two corners with two further single head seams. Thereafter, the lateral straight eye muscle 13 is again pulled forwardly by means of the holding thread and is then attached to its original root over annular portion 32 by means of muscle seems. Subsequently, the conjunctiva is then again attached by means of a few single head seams and the rein thread is removed. After the position of the chip and the fundus conditions have been examined by means of direct and indirect ophthalmoscopy, an ointment dressing is applied.

What is claimed is:

1. A retina implant to be implanted into an eye having an eyeball with an exterior and an interior, a sclera, a lens, and a retina, the implant comprising:
    a chip adapted to be implanted into said interior of said eye being in contact with said retina, said chip, when in an implanted condition, having a plurality of pixel elements on a side thereof facing said lens for receiving an image projected onto said retina, as well as a plurality of electrodes for stimulating cells of said retina, said electrodes being located on said side of said chip having said pixel elements thereon, such that said chip is adapted to be implanted into a subretinal space of said eye;
    a receiver coil for inductively coupling thereinto electromagnetic energy, said receiver coil being coupled to a means for converting an alternating voltage induced into said receiver coil in a direct voltage suited for supplying said chip, said receiver coil being configured as a component separate from said chip, and configured for being positioned on said eyeball outside said sclera, said chip being connected to said receiver coil via a connecting lead which, in said implanted condition, interconnects said interior and said exterior of said eye ball.

2. The retina implant of claim 1, wherein said receiver coil, said chip as well as connecting leads leading to said chip are housed within a flat plastic material body.

3. The retina implant of claim 1, wherein said converting means is configured as a unit separate from said chip.

4. The retina implant of claim 2, wherein said plastic material body comprises an annular portion having a central opening, said annular portion being adjoined by a flat extension.

5. The retina implant of claim 4, wherein said annular portion is dimensioned as to enclose a lateral straight eye muscle rudiment.

6. The retina implant of claim 5, wherein said converting means is comprised within said plastic material body in a position adjacent said receiver coil.

7. The retina implant of claim 3, wherein said receiver coil comprises windings integrated into said annular portion.

8. The retina implant of claim 7, wherein said windings are configured in a spiralled pattern.

9. The retina implant of claim 4, wherein said annular portion is subdivided into a plurality of sections in a circumferential direction, said sections being separated from each other by gaps and being electrically and mechanically interconnected.

10. The retina implant of claim 8, wherein said sections are interconnected with each other by a fin in a radial direction.

11. The retina implant of claim 8, wherein said sections adhere each other in a spiralled configuration.

12. The retina implant of claim 8, wherein said sections are molded together in a spheric body having a curvature being adapted to a surface of said eyeball.

13. The retina implant of claim 1, wherein strain relief means are provided at least between said converter means and a connection lead leading to said chip or to said receiver coil.

14. The retina implant of claim 1, wherein said receiver coil has a number of windings of between 50 and 200.

15. The retina implant of claim 14, wherein said receiver coil has between 90 and 110 windings.

16. The retina implant of claim 1, wherein said receiver coil has an outer diameter of between 12 and 20 mm and an inner diameter at a central opening thereof of between 8 and 16 mm.

17. The retina implant of claim 4, wherein said flat extension is provided with a plurality of perforations.

18. The retina implant of claim 4, wherein said chip is imbedded in said flat extension.

19. The retina implant of claim 2, wherein said flat plastic material body is provided with lugs for affixing said plastic material body to said eyeball.

20. The retina implant of claim 1, wherein said converter means comprises means for processing an information signal transmitted together with said electromagnetic energy.

21. The retina implant of claim 20, wherein said information signal is a reference signal indicative for ambient brightness.

22. A method for manufacturing a retina implant having a chip for subretinal implantation, and comprising a receiver coil inductively coupling electromagnetic energy for thereinto, means for converting an alternating voltage induced into said receiver coil into a direct voltage suited for supplying said chip, the method comprising the steps of:
    a) manufacturing a flat plastic material body having an annular portion with a central opening, said annular portion being adjoined by a flat extension;
    b) depositing metallic strip conductors on a surface of said annular portion in a spiralled configuration for making windings of said receiver coil and for creating connecting leads between said receiver coil, said converter means, and said chip;
    c) affixing said chip and said converter means to said plastic material body; and
    d) depositing an isolation layer over said metallic strip conductors.

23. The method of claim 22, wherein said flat plastic material body is generated on an auxiliary substrate and is then separated therefrom.

24. The method of claim 23, wherein said strip conductors are generated on said surface by means of a thin film process and are then micro structured photolithographically.

25. The method of claim 22, wherein said converter means is affixed to said plastic material body by gluing.

26. The method of claim 22, wherein said converter means is affixed to said plastic material body by bonding with said metallic strip conductors.

27. The method of claim 22, wherein said converter means is affixed to said plastic material body by injection-molding in a plastic material mass.

28. The method of claim 22, wherein said annular portion is subdivided into a plurality of sections in a circumferential direction, said sections being separated from each other by gaps and being electrically and mechanically interconnected.

29. The method of claim 28, wherein said sections are molded together in a spherical calotte body having a curvature being adapted to a surface of said eyeball.

30. The method of claim 22, wherein said plastic material body is manufactured from polyimide, polymethacrylate (PMMA) or epoxy resin.

31. The method of claim 30, wherein said plastic material body together with said isolation layer is manufactured with a thickness of between 5 and 15 micrometers.

32. The method of claim 22, wherein said plastic material body together with said isolation layer is manufactured with a thickness of between 5 and 15 micrometers.

33. The method of claim 22, wherein said metallic strip conductors are generated with a thickness (X) of between 0.5 to 2 micrometers.

34. The method of claim 33, wherein said metallic strip conductors are generated with a thickness (X) of between 0.8 to 1.2 micrometers.

35. The method of claim 22, wherein said flat plastic material body is provided with perforations in an area of said flat extension.

36. A method of stimulating a retina of an eye comprising
positioning a light sensitive chip having pixel elements and electrodes for stimulating cells on the same side of the chip into a subretinal space so as to face the lens of the eye;
connecting the chip to receiver coils positioned on the outer surface of the eyeball;
transmitting electromagnetic energy to the receiver coils; and
rectifying the received electromagnetic energy so as to power the chip such that the chip provides amplified stimulus signals corresponding to the incident light energy to the retina.

37. The method of claim 36, further comprising further comprising processing of reference signals transmitted together with said electromagnetic energy, said reference signals indicative of ambient brightness, for adapting an output signal amplitude of the chip under varying ambient light intensity or brightness conditions.

38. The method of claim 36, further comprising forming the receiver coils as part of an annular member and at least partially affixing the receiver coils to the outer surface of the eyeball by passing eye muscle through an opening in the annular member.

39. The method of claim 38, comprising forming the annular member from a plurality of flexibly attached sections.

40. The method of claim 36, comprising forming the receiver coils so as to conform to the contour of the outer surface of the eyeball.

41. The method of claim 36, comprising forming the chip and receiver coils as a one-piece retina implant assembly adapted to be positioned partially inside and partially on the outer surface of the eye.

42. The method of claim 41, comprising joining the chip and the receiver coils with a strain relief.

43. A retina implant assembly adapted for implantation into an eye, the eye comprising a retina with a subretinal region, a lens, and an outer surface, the implant comprising:
a chip adapted to be implanted into the subretinal region wherein the chip comprises a plurality of pixel elements arranged so as to face the lens when the chip is in an implanted condition and a plurality of electrodes arranged on the same side of the chip as the pixel elements so as to stimulate the retina;
a receiver coil adapted to inductively couple incident electromagnetic radiation thereinto wherein the receiver coil is configured as a separate component from the chip and is positioned on the outer surface of the eye;
a converter in communication with the receiver coil so as to convert alternating current induced in the receiver coil into a direct current and providing the direct current to the chip; and
a connecting lead interconnecting the chip and the receiver coil.

44. The assembly of claim 43, wherein the interconnecting lead comprises a strain relief.

45. A retina implant to be implanted into an eye having an eyeball with an exterior and an interior, a sclera, a lens, and a retina, the implant comprising:
a chip adapted to be implanted into said interior of said eye being in contact with said retina, said chip, when in an implanted condition, having a plurality of pixel elements on a side thereof facing said lens for receiving an image projected onto said retina, as well as a plurality of electrodes for stimulating cells of said retina, said electrodes being located on said side of said chip having said pixel elements thereon, such that said chip is adapted to be implanted into a subretinal space of said eye;
a receiver coil for inductively coupling thereinto electromagnetic energy, said receiver coil being coupled to a means for converting an alternating voltage induced into said receiver coil in a direct voltage suited for supplying said chip, said receiver coil being configured as a component separate from said chip, and configured for being positioned on said eyeball outside said sclera, said chip being connected to said receiver coil via a connecting lead which, in said implanted condition, interconnects said interior and said exterior of said eye ball; and
a generally flat, plastic material body housing the receiver coil, the chip, and the connecting leads.

46. A retina implant to be implanted into an eye having an eyeball with an exterior and an interior, a sclera, a lens, and a retina, the implant comprising:
a chip adapted to be implanted into said interior of said eye being in contact with said retina, said chip, when in an implanted condition, having a plurality of pixel elements on a side thereof facing said lens for receiving an image projected onto said retina, as well as a plurality of electrodes for stimulating cells of said retina, said electrodes being located on said side of said chip having said pixel elements thereon, such that said chip is adapted to be implanted into a subretinal space of said eye;
a receiver coil for inductively coupling thereinto electromagnetic energy, said receiver coil being coupled to a means for converting an alternating voltage induced into said receiver coil in a direct voltage suited for supplying said chip, said receiver coil being configured as a component separate from said chip, and configured for being positioned on said eyeball outside said sclera, said chip being connected to said receiver coil via a connecting lead which, in said implanted condition, interconnects said interior and said exterior of said eye ball; and
strain relief means provided between said means for converting and at least one of the chip and the receiver coil.

47. A retina implant to be implanted into an eye having an eyeball with an exterior and an interior, a sclera, a lens, and a retina, the implant comprising:
a chip adapted to be implanted into said interior of said eye being in contact with said retina, said chip, when in an implanted condition, having a plurality of pixel elements on a side thereof facing said lens for receiving an image projected onto said retina, as well as a plurality of electrodes for stimulating cells of said retina, said electrodes being located on said side of said chip having said pixel elements thereon, such that said chip is adapted to be implanted into a subretinal space of said eye; and a receiver coil for inductively coupling thereinto electromagnetic energy and having an outer diameter of between 12 and 20 mm and an inner diameter at a central opening of the receiver coil of between 8 and 16 mm, said receiver coil being coupled to a means for converting an alternating voltage induced into said receiver coil in a direct voltage suited for supplying said chip, said receiver coil being configured as a component separate from said chip, and configured for being positioned on said eyeball outside said sclera, said chip being connected to said receiver coil via a connecting lead which, in said implanted condition, interconnects said interior and said exterior of said eye ball.

48. A retina implant assembly adapted for implantation into an eye, the eye comprising a retina with a subretinal region, a lens, and an outer surface, the implant comprising:

a chip adapted to be implanted into the subretinal region wherein the chip comprises a plurality of pixel elements arranged so as to face the lens when the chip is in an implanted condition and a plurality of electrodes arranged on the same side of the chip as the pixel elements so as to stimulate the retina;

a receiver coil adapted to inductively couple incident electromagnetic radiation thereinto wherein the receiver coil is configured as a separate component from the chip and is positioned on the outer surface of the eye;

a converter in communication with the receiver coil so as to convert alternating current induced in the receiver coil into a direct current and providing the direct current to the chip; and a connecting lead comprising a strain relief and interconnecting the chip and the receiver coil.

49. A method of stimulating a retina of an eye comprising positioning a light sensitive chip into a subretinal space so as to face the lens of the eye;

forming receiver coils as part of an annular member;

at least partially affixing the receiver coils to the outer surface of the eye by passing eye muscle through an opening in the annular member;

connecting the chip to the receiver coils;

transmitting electromagnetic energy to the receiver coils; and rectifying the received electromagnetic energy so as to power the chip such that the chip provides amplified stimulus signals corresponding to the incident light energy to the retina.

* * * * *

UNITED STATES PATENT AND TRADEMARK OFFICE
CERTIFICATE OF CORRECTION

PATENT NO. : 6,847,847 B2
DATED : January 25, 2005
INVENTOR(S) : Nisch et al.

It is certified that error appears in the above-identified patent and that said Letters Patent is hereby corrected as shown below:

<u>Title page,</u>
Item [57], ABSTRACT,
Line 6, delete "implants" and insert -- implant --.

<u>Column 10,</u>
Line 27, after "energy" delete "for".

<u>Column 11,</u>
Lines 29-30, before "processing" delete "further comprising".

Signed and Sealed this

Eighteenth Day of April, 2006

JON W. DUDAS
*Director of the United States Patent and Trademark Office*